United States Patent
White et al.

(10) Patent No.: US 10,443,086 B2
(45) Date of Patent: Oct. 15, 2019

(54) METHODS, DEVICES AND SYSTEMS FOR EMULSION/DROPLET PCR

(71) Applicant: Canon U.S. Life Sciences, Inc., Rockville, MD (US)

(72) Inventors: Ian M. White, Ellicott City, MD (US); Kunal Pandit, Laurel, MD (US); Srinivasa Raghavan, Silver Spring, MD (US)

(73) Assignee: University of Maryland, College Park, College Park, MD (US)

( * ) Notice: Subject to any disclaimer, the term of this patent is extended or adjusted under 35 U.S.C. 154(b) by 470 days.

(21) Appl. No.: 14/586,564

(22) Filed: Dec. 30, 2014

(65) Prior Publication Data
US 2015/0184151 A1    Jul. 2, 2015

Related U.S. Application Data

(60) Provisional application No. 61/922,422, filed on Dec. 31, 2013.

(51) Int. Cl.
| | | |
|---|---|---|
| *C12Q 1/68* | (2018.01) | |
| *C12Q 1/6806* | (2018.01) | |
| *C12N 15/10* | (2006.01) | |
| *G01N 13/02* | (2006.01) | |

(52) U.S. Cl.
CPC ....... *C12Q 1/6806* (2013.01); *C12N 15/1075* (2013.01); *G01N 13/02* (2013.01); *G01N 2013/0241* (2013.01)

(58) Field of Classification Search
CPC .................................................. C12Q 1/6806
USPC ......................................... 435/6.1, 6.12, 91.1
See application file for complete search history.

(56) References Cited

U.S. PATENT DOCUMENTS

| | | |
|---|---|---|
| 5,783,525 A | 7/1998 | Blanco et al. |
| 2006/0068390 A1* | 3/2006 | Tillett .......... C12Q 1/6844 435/6.14 |
| 2010/0173394 A1 | 7/2010 | Colston, Jr. et al. |
| 2011/0076751 A1 | 3/2011 | Fabis et al. |
| 2014/0080717 A1* | 3/2014 | Li .......... C12Q 1/6855 506/2 |

OTHER PUBLICATIONS

F. Moltzahn et al., "Microfluidic-Based Multiplex qRT-PCR Identifies Diagnostic and Prognostic microRNA Signatures in the Sera of Prostate Cancer Patients," Cancer Res. 2011, 71, 550-560.
M.C. Strain et al., "Highly Precise Measurement of HIV DNA by Droplet Digital PCR," PLoS ONE 2013, 8, e55943.
(Continued)

*Primary Examiner* — Jezia Riley
(74) *Attorney, Agent, or Firm* — Rothwell, Figg, Ernst & Manbeck, P.C.

(57) ABSTRACT

The present invention relates generally to the use of a class of surfactants for emulsion and droplet polymerase chain reaction ("PCR") mixtures. The class of surfactants consists of those having the chemical formula $R-(OCH_2CH_2)_n-OH$, wherein R is an alkyl group consisting of 12 to 18 carbons and n is 2 to 25. The present invention also relates to methods, devices, systems, and kits incorporating the above-described class of surfactants.

14 Claims, 9 Drawing Sheets
Specification includes a Sequence Listing.

(56) References Cited

OTHER PUBLICATIONS

P. Liu et al., "Integrated DNA purification, PCR, sample cleanup, and capillary electrophoresis microchip for forensic human identification," Lab. Chip 2011, 11, 1041-1048.
J.A. Lounsbury et al., "From sample to PCR product in under 45 minutes: a polymeric integrated microdevice for clinical and forensic DNA analysis," Lab. Chip 2013, 13, 1384-1393 (abstract only).
D. Pekin et al., "Quantitative and sensitive detection of rare mutations using droplet-based microfluidics," Lab. Chip 2011, 11, 2156-2166.
P. Neuzil et al., "Ultra fast miniaturized real-time PCR: 40 cycles in less than six minutes," Nucleic Acids Res. 2006, 34, e77.
N.R. Beer et al., "On-Chip, Real-Time, Single-Copy Polymerase Chain Reaction in Picoliter Droplets," Anal. Chem. 2007, 79, 8471-8475.
S.L. Angione et al., "Real-Time Droplet Dna Amplification with a New Tablet Platform,"Anal. Chem., 2012, 84, 2654-2661 (abstract only).
F.C. Lawyer et al., "High-level Expression, Purification, and Enzymatic Characterization of Full-length Thermus aquaticus DNA Polymerase and a Truncated Form Deficient in 5' to 3' Exonuclease Activity," Genome Res. 1993, 2, 275-287.
F. Wang et al., "Performance of nanoliter-sized droplet-based microfluidic PCR," Biomed. Microdevices 2009, 19 pages.
A.C. Hatch et al., "1-Million droplet array with wide-field fluorescence imaging for digital PCR," Lab. Chip 2011, 11, 3838-3845.
F. Diehl et al., "BEAMing: single-molecule PCR on microparticles in water-in-oil emulsions," Nat. Methods 2006, 3, 551-559 (abstract only).
R. Williams et al., "Amplification of complex gene libraries by emulsion PCR," Nat. Methods 2006, 3, 545-550.

\* cited by examiner

METHODS, DEVICES AND SYSTEMS FOR EMULSION/DROPLET PCR

CROSS REFERENCE TO RELATED APPLICATIONS

The present application claims the benefit of priority to U.S. Provisional Application No. 61/922,422, filed on Dec. 31, 2013, which is incorporated herein by reference in its entirety.

TECHNICAL FIELD

The present invention relates generally to surfactants for emulsion and droplet polymerase chain reaction ("PCR"). The present invention also relates to methods, devices, systems, and kits incorporating those surfactants.

SEQUENCE SUBMISSION

The present application is being filed along with a Sequence Listing in electronic format. The Sequence Listing is entitled 3400-265_ST25.txt, created on Dec. 12, 2014 and is 1 kb in size. The information in the electronic format of the Sequence Listing is incorporated herein by reference in its entirety.

BACKGROUND

PCR is a biochemical technique used to amplify, quantify, and identify specific genes related to cancers, infectious diseases, forensics, and hereditary disorders. Exemplary references discussing PCR, which are incorporated by reference in their entirety, include: F. Moltzahn et al., Cancer Res. 2011, 71, 550-560; M. C. Strain et al., PLoS ONE 2013, 8, e55943; P. Liu et al., Lab. Chip 2011, 11, 1041-1048; J. A. Lounsbury et al., Lab. Chip 2013, 13, 1384-1393; and D. Pekin et al., Lab. Chip 2011, 11, 2156-2166. PCR is commonly performed in central laboratory environments and can involve thermocycling of 20-50 μL samples in well plates. The process to complete PCR, including sample preparation, can take several hours and require a number of manual steps. The duration of PCR from sample preparation to DNA analysis can be reduced by integrating laboratory functions in micro total analysis systems.

An important and widely used element of micro total analysis systems is the droplet PCR component. Ultrafast droplet PCR can be performed with integrated heaters, wherein up to 40 thermal cycles can be conducted in less than six minutes. One such reference discussing this process, which is incorporated by reference in its entirety, is P. Neuzil, Nucleic Acids Res. 2006, 34, e77.

In droplet PCR, droplet microfluidics is used to monodispersly portion PCR reaction mixtures into microreactors surrounded by an oil phase. That is, PCR reaction mixtures can be formed as an aqueous droplet, which are surrounded by an oil phase. Typically, the droplets can differ in size, but are typically on the order of nanoliters or picoliters. At the larger end of this size range, DNA is quantified using a cycle threshold calibration curve. DNA has been absolutely quantified using a popular variation of PCR termed "digital PCR" by using picoliter droplets. The initial average DNA copy number per droplet in digital PCR is less than 1, implying a Poisson distribution with 0 or 1 copy in most droplets. One such reference discussing this process, which is incorporated by reference in its entirety, is N. R. Beer et al., Anal. Chem. 2007, 79, 8471-8475. In digital PCR, after thermocycling, only droplets that contain the target DNA fluoresce. The number of fluorescent and nonfluorescent droplets is counted to absolutely quantify the amount of target DNA according to Poisson statistics. Digital PCR is extremely useful and has been shown to quantify extremely rare targets, such as HIV DNA in infected patients undergoing effective treatment. See M. C. Strain et al., supra.

Though impactful, droplet PCR is in need of technical improvement. For example, as discussed in S. L. Angione et al., Anal. Chem., 2012, 84, 2654-2661, which is incorporated by reference in its entirety, microreactors less than microliters in volume are impaired by surface effects. While it is desirable to have an increase in surface area relative to the volume of the droplet for quick transfer, this presents several potential problems. Irreversible adsorption of amphiphilic proteins occurs as the droplet size becomes smaller and the ratio of the surface area to the volume increases. This irreversible adsorption of proteins to hydrophobic interfaces hinders microfluidic assay.

The adsorption of proteins is particularly problematic with droplet PCR, which makes use of Taq polymerase (Taq Pol) to catalyze the reaction. Taq Pol, an enzyme derived from thermophilic bacteria, is especially prone to absorption at hydrophobic interfaces because a large volume fraction of it is hydrophobic. The aliphatic index characterizes the relative hydrophobic volume of a protein and, in general, thermophilic bacterial proteins have large relative hydrophobic volumes to aide in structural stability. The aliphatic index of Taq Pol is 98.6 (compared to the aliphatic index of BSA, which is 76.1). As discussed in F. C. Lawyer et al., Genome Res. 1993, 2, 275-287, which is incorporated by reference in its entirety, Taq Pol is incredibly stable; even at DNA melting temperatures of 95° C., the half-life of Taq Pol is 45 to 50 min. Thus, less stable proteins used in droplet microfluidics would sample a larger structural space, resulting in the interaction with and irreversible denaturing of the less stable proteins on the hydrophobic surface. Thus, adsorption is exacerbated when using unstable proteins in microfluidic droplets.

Many techniques have been employed to overcome the adsorption of proteins, but these methods have several different flaws. As discussed in S. L. Angione et al., Anal. Chem., 2012, 84, 2654-2661, which is incorporated by reference in its entirety, one technique employed to overcome the adsorption of proteins is to increase the Taq Pol concentration in an attempt to replace the adsorbed enzyme. This technique, however, is a wasteful solution that can require up to seven times the concentration of bulk PCR for optimal performance. The technique is further described in F. Wang et al., Biomed. Microdevices 2009, which is incorporated by reference in its entirety.

Another technique, as discussed in A. C. Hatch et al., Lab. Chip 2011, 11, 3838-3845, which is incorporated by reference in its entirety, is to increase the amount of surfactant used in the system. In addition to stabilizing droplets, large amounts of surfactant can competitively bind to the hydrophobic interface and reduce Taq Pol adsorption, though excessive surfactant can inhibit PCR. Similarly, bovine serum albumin may be included in the PCR mixture to competitively bind to the interface. Usually, both methods are employed simultaneously to create an emulsion, but as discussed in F. Diehl et al., Nat. Methods 2006, 3, 551-559 and R. Williams et al., Nat. Methods 2006, 3, 545-550, which are incorporated by reference in their entirety, for successful PCR, the emulsion must be generated on ice. Yet another technique employs the use of fluorinated oils and surfactants with Taq Pol at room temperature to create droplets for digital PCR. This technique, however, requires fluorocarbon specialty chemicals, which increases costs and concerns for the environment.

In view of the above, there is a need for PCR methods, systems, and kits that overcome the issues associated with protein adsorption in microfluidics that do not suffer from the above described flaws.

SUMMARY

In one aspect, the present invention relates to a droplet or emulsion PCR comprising an aqueous droplet. In one embodiment, the aqueous droplet includes a polymerase chain reaction mixture, an oil phase, and a surfactant having Formula I:

R—(OCH$_2$CH$_2$)$_n$—OH, wherein R is an alkyl group consisting of 12 to 18 carbons and n is 2 to 25.

In some embodiments, the polymerase chain reaction mixture may comprise a polymerase, a primer, nucleotides, and a template nucleic acid. In some embodiments, the surfactant can be one selected from the group consisting of laureth-4, laureth-23, ceteth-2, ceteth-20, ceteareth-12, ceteareth-20, ceteareth-25, steareth-2, steareth-10, steareth-20, steareth-21, oleth-2, oleth-5, oleth-10, and oleth-20.

In another aspect, the present invention relates to methods for preparing a mixture for droplet or emulsion PCR. In one embodiment, the method includes forming an aqueous droplet comprising a polymerase chain reaction mixture. In another embodiment, the method includes surrounding the aqueous droplet with an oil phase. In another embodiment, the method includes adding a surfactant having Formula I:

R—(OCH$_2$CH$_2$)$_n$—OH, wherein R is an alkyl group consisting of 12 to 18 carbons and n is 2 to 25. In one embodiment, the polymerase chain reaction mixture may comprise a polymerase, a primer, nucleotides, and a template nucleic acid. In some embodiments, the added surfactant can be selected from the group consisting of laureth-4, laureth-23, ceteth-2, ceteth-20, ceteareth-12, ceteareth-20, ceteareth-25, steareth-2, steareth-10, steareth-20, steareth-21, oleth-2, oleth-5, oleth-10, and oleth-20.

In yet another aspect, the present invention also relates to methods for determining the capability of a surfactant for droplet or emulsion PCR. In one embodiment, the method includes preparing an aqueous droplet comprising Taq polymerase. In another embodiment, the method includes suspending the aqueous droplet in an oil phase comprising a dissolved surfactant. In a further embodiment, the method includes forming a hanging drop of the aqueous droplet suspended in the oil phase. In an additional embodiment, the method includes measuring a property of the hanging drop. In some embodiments, the measured property is the interfacial tension of the hanging drop, which is determined using equation: $\gamma = 3.17\, g\Delta p D_e^{-0.68} D_s^{2.68}$, wherein $D_e$ is the largest width of the drop, $D_s$ is the width of the drop at the distance $D_e$, g is the acceleration due to gravity, 9.8 m/s$^2$, and $\Delta p$ is the difference in density between the aqueous droplet and the oil phase.

BRIEF DESCRIPTION OF THE DRAWINGS

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein. In the drawings, like reference numbers indicate identical or functionally similar elements.

DETAILED DESCRIPTION OF PREFERRED EMBODIMENTS

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The present invention relates to droplet and emulsion PCR. As understood by a person of ordinary skill in the art, droplet and emulsion PCR are commonly used techniques for the amplification and detection of nucleic acid sequences in integrated microsystems. In one aspect, the present invention relates to a droplet or emulsion PCR mixture. The droplet or emulsion PCR mixture is a mixture in which the PCR reaction is carried out. The aqueous droplet can be on the order of nanoliters to picoliters in size. For example, the aqueous droplets can have a diameter of, in a non-limiting example, 20±2 μm, resulting in an aqueous droplet that is approximately 4 picoliters. Other droplet sizes may also be used.

In certain embodiments of the present invention, the aqueous droplet comprises a PCR mixture. In some embodiments, the PCR mixture may include one or more of a polymerase, a primer, nucleotides, a template nucleic acid, and a fluorescent die. In some embodiments, the PCR mixture includes Taq polymerase (Taq Pol) as the polymerase.

In some embodiments, the droplet or emulsion PCR mixtures of the present invention further comprise an oil phase. In certain embodiments of the present invention, the oil phase consists of a mineral oil solution. In exemplary embodiments of the present invention, the oil phase surrounds the aqueous droplet.

In conventional droplet or emulsion PCR, hydrophobic components of proteins bind to the oil phase at the surface of the aqueous droplet, resulting in the removal of hydrophobic components. During droplet formation, the adsorption of proteins to the interface can begin immediately. Initially, the adsorption is diffusion controlled, wherein a clean interface adsorbs surfactants and proteins as they diffuse from within the droplet or surrounding continuous phase. Interfacial tension between the continuous phase and droplet phase may decrease proportionally to the number of amphiphiles bound to the interface. Once an appreciable film of proteins is formed, an energy barrier to create space within the interface can resist adsorption. The decrease in interfacial tension at this stage is a result of the adsorption of proteins, as well as the molecular rearrangement within the film (e.g., proteins denaturing at the surface).

In certain embodiments of the present invention, a surfactant is included in the droplet or emulsion PCR mixture. In some embodiments, the surfactant can be added to the oil phase and can surround the surface of the aqueous droplet. In one embodiment, the surfactant can be added to the oil phase before the aqueous droplet is surrounded by or suspended in the oil phase. In another embodiment, the surfactant can be added to the oil phase after the aqueous droplet is surrounded by or suspended in the oil phase. The surfactant can act to prevent the interaction of hydrophobic components with the oil phase. Further, the surfactant can act to stabilize the aqueous droplet. The use of the surfactants described herein result in more efficient amplification during droplet or emulsion PCR.

In one embodiment, the surfactant has Formula 1:

wherein R is an alkyl group consisting of 12 to 18 carbons and n is 2 to 25. In some embodiments, suitable surfactants include laureth-4, laureth-23, ceteth-2, ceteth-20, ceteareth-12, ceteareth-20, ceteareth-25, steareth-2, steareth-10, steareth-20, steareth-21, oleth-2, oleth-5, oleth-10, and oleth-20. In one embodiment, the surfactant is laureth-4. These surfactants are available under the tradename Brij (e.g., Brij L, Brij C, Brij CS, Brij S, and Brij O) from Croda Europe Ltd. (East Yorkshire, England). The above-described surfactants are alkyl polyglycol ethers derived from a variety of straight and branched chain alcohols produced by reacting ethylene oxide with fatty alcohols.

Figure 1:
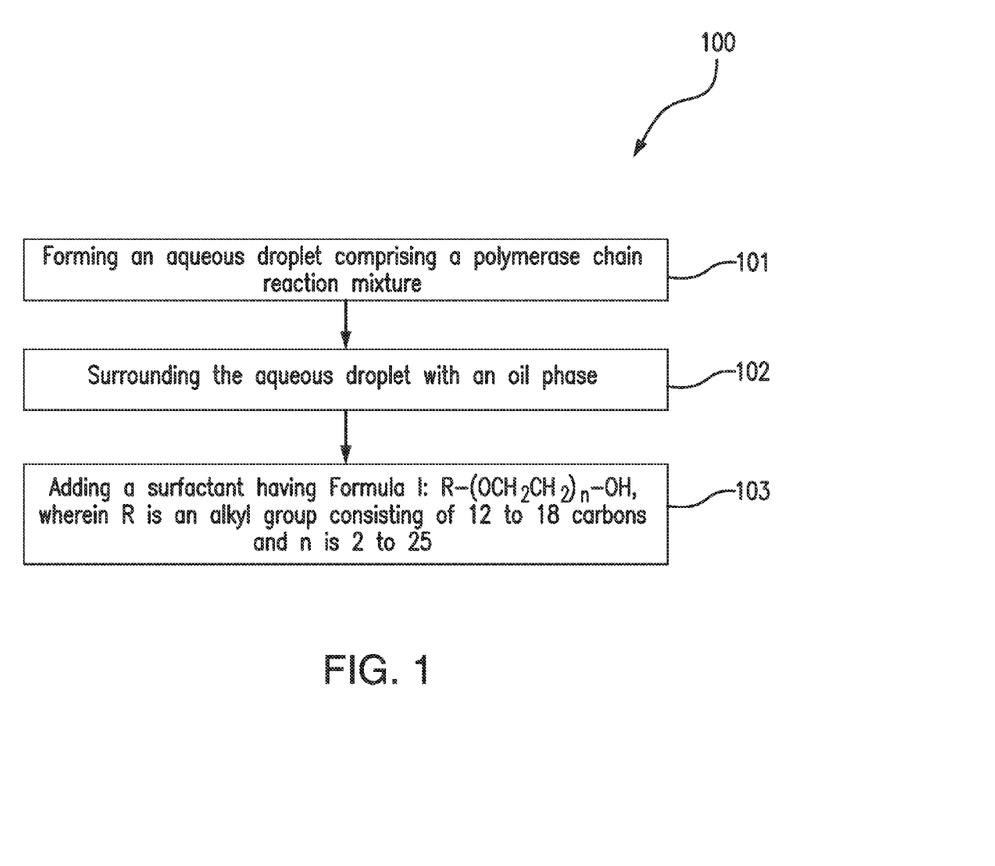
FIG. 1 is a flow chart of a method for preparing a mixture for droplet or emulsion PCR in accordance with an embodiment of the present invention.

In another aspect, the present invention relates to methods for preparing droplet or emulsion PCR mixtures. FIG. 1 is a flow chart of method 100 for preparing a mixture for droplet or emulsion PCR in accordance with one embodiment of the present invention. Method 100 includes forming an aqueous droplet comprising a PCR mixture (step 101). The droplet or emulsion PCR mixture is a mixture in which the PCR reaction is carried out. In some embodiments, the aqueous droplet comprises a PCR mixture, which may include one or more of a polymerase, a primer, nucleotides, a template nucleic acid, and a fluorescent die. In some embodiments, the PCR mixture includes Taq Pol as the polymerase.

In a non-limiting embodiment, the aqueous droplets can be formed in a polydimethylsiloxane (PDMS) microfluidic chip using flow focusing geometry. When preparing the aqueous droplets, the aqueous droplets can be captured as a single droplet within a well. The well can be one suitable for carrying out droplet or emulsion PCR.

In some embodiments, method 100 further includes surrounding the aqueous droplet with an oil phase (step 102). In some embodiments, the oil phase comprises a mineral oil solution. In one embodiment, the oil phase can be present in a well in which an aqueous droplet is introduced. Alternatively, in a second embodiment, the oil phase can be added to an aqueous droplet resulting in the oil phase surrounding the aqueous droplet.

In other embodiments, method 100 further includes adding a surfactant having the Formula I:

wherein R is an alkyl group consisting of 12 to 18 carbons and n is 2 to 25 (step 103). In some embodiments, the surfactant is one selected from the group consisting of laureth-4, laureth-23, ceteth-2, ceteth-20, ceteareth-12, ceteareth-20, ceteareth-25, steareth-2, steareth-10, steareth-20, steareth-21, oleth-2, oleth-5, oleth-10, and oleth-20. In one embodiment, the surfactant is laureth-4. In one embodiment, the surfactant can be added to the oil phase prior to the introduction of the aqueous droplet. Alternatively, in a second embodiment, the surfactant can be added to the oil phase after the aqueous droplet has been surrounded by the oil phase.

In certain embodiments, the aqueous droplets can be used for emulsion or droplet PCR. In some embodiments, a plurality of aqueous droplets is formed. In some embodiments, only a portion of the plurality of aqueous droplets comprises a template. In some embodiments, the template is randomly distributed in certain aqueous droplets, while other aqueous droplets do not comprise a template.

In certain embodiments, the method can further include steps involved in droplet or emulsion PCR. For example, the droplet or emulsion PCR mixture can be hot started. In one embodiment, the mixtures are hot started at 95° C. for a period of time. The droplet or emulsion PCR mixture can then be thermocycled for a number of cycles. In some embodiments, each thermocycle can an annealing step, an extension step, and a melting step. For example, in one embodiment, each thermocycle can consist of 30 seconds at 55° C. for annealing, 30 seconds at 72° C. for extension, and 30 seconds at 95° C. for melting. In certain exemplary embodiments, real time amplification results are obtained. For example, real time amplification results can be obtained by exciting droplets using a light emitting diode (LED). In some embodiments, the fluorescence emission can be captured with a charged couple device (CCD). In some embodiments, certain aqueous droplets will produce a difference in fluorescence emission than other aqueous droplets. In some embodiments wherein a plurality of aqueous droplets are formed, some with a template and others without a template, the fluorescence emission for the aqueous droplets with the template can differ from the fluorescence emission for the aqueous droplets without the template.

Figure 2:
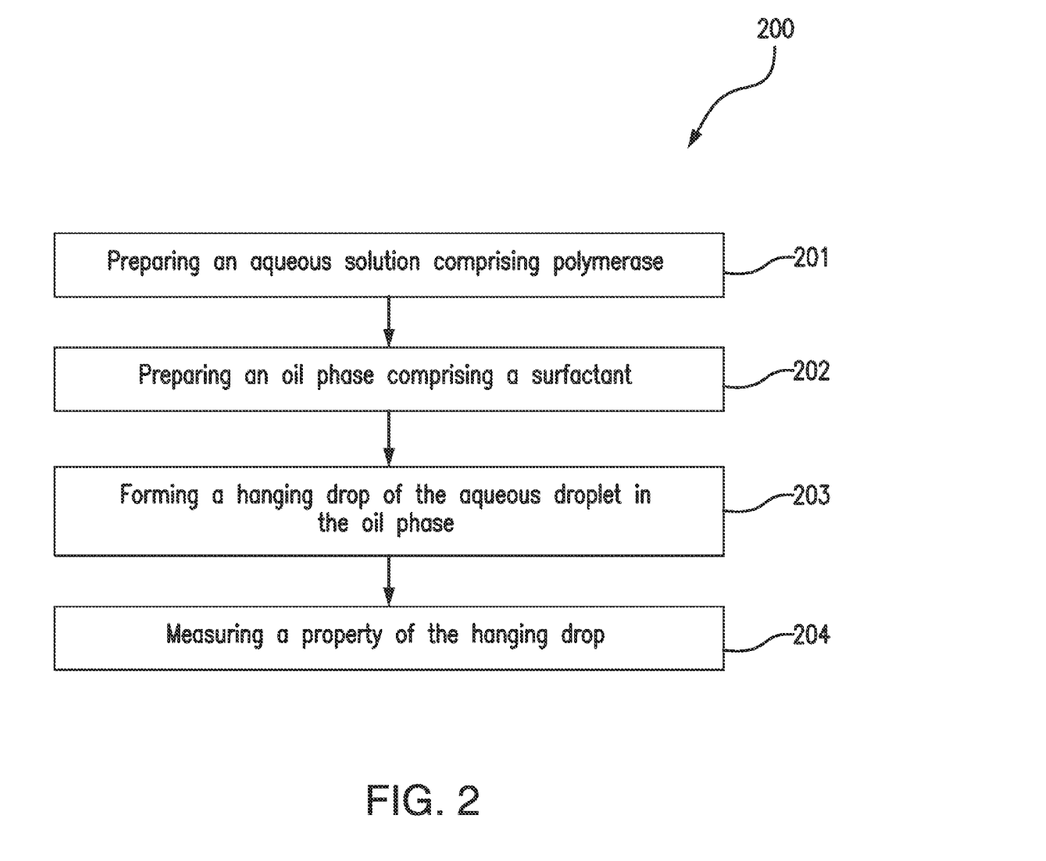
FIG. 2 is a flow chart of a method for determining the capability of a surfactant for droplet or emulsion PCR in accordance with an embodiment of the present invention.

In another aspect, the present invention includes a method of measuring adsorption and loss of polymerase at a droplet surface for surfactant-oil combinations. FIG. 2 is a flow chart of method 200 for determining the capability of a surfactant for droplet or emulsion PCR in accordance with one embodiment of the present invention. The method allows for identification of superior surfactants for use in emulsion and droplet PCR. In contrast, traditional surfactant selection for emulsion and droplet PCR relies on trial and error.

In certain embodiments, the pendant drop technique is used to determine the ability of a surfactant to prevent polymerase loss from the PCR reaction. Method 200 includes forming an aqueous droplet comprising a polymerase (step 201). In certain embodiments, the polymerase is Taq Pol. The concentration of Taq Pol is non-limiting and can vary. In some embodiments, the aqueous droplet comprises a concentration of Taq Pol in the amount of 0 to 8×, wherein 1× is 0.025 U/µL. In other embodiments, the aqueous droplet comprises one or more of a PCR buffer, a primer, nucleotides, a template nucleic acid, and a fluorescent die. In certain embodiments, the aqueous droplet is stored on ice.

In some embodiments, method 200 further includes preparing an oil phase comprising a surfactant (step 202). In one embodiment, the oil phase comprises mineral oil. For example, the oil phase can comprise a stock mineral oil solution of the surfactant cetyl PEG/PPG-10/1 dimethicone sold under the name ABIL EM90 by Evonik Industries (Germany). In another embodiment, the oil phase can comprise a stock mineral oil solution of a surfactant having Formula I described herein. In one embodiment, the surfactant is laureth-4. In one embodiment, the oil phase can comprise a surfactant in varying concentrations. In some embodiments, the oil phase can comprise a stock mineral oil solution of 1.5% (w/w) ABIL EM90 or 0.5% (w/w) laureth-4. In some embodiments, the mineral oil solutions can be preheated and maintained at a temperature using a water bath. In one embodiment, the mineral oil solutions can be preheated and maintained at a temperature of about 55° C.

Figure 3:
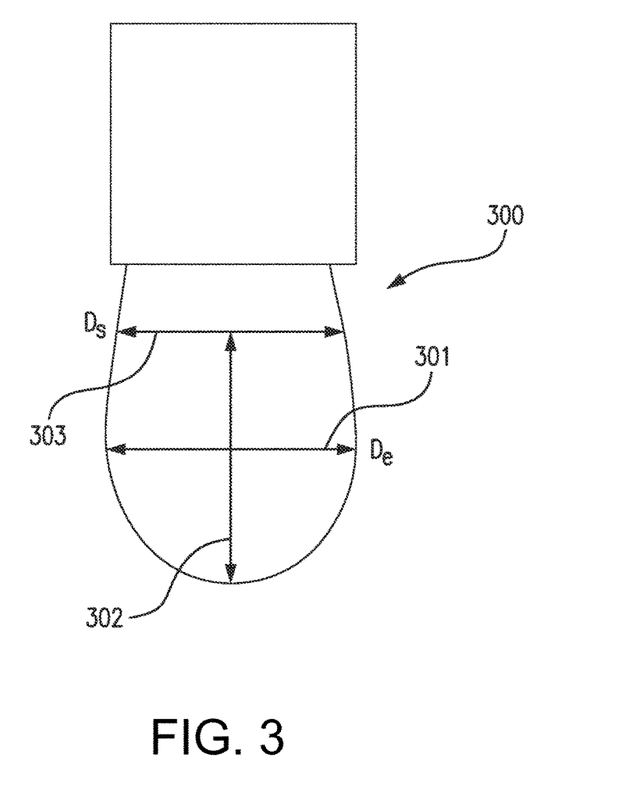
FIG. 3 illustrates an exemplary hanging droplet in accordance with an embodiment of the present invention.

In some embodiments, method 200 further includes forming a hanging drop of the aqueous droplet in the oil phase (step 203). In certain embodiments, the hanging drop is the largest non-spherical drop that can be formed without pinching off the aqueous droplet suspended in the oil phase. FIG. 3 illustrates an exemplary hanging drop 300. In one embodiment, the hanging drop can be a single droplet formed from the end or tip of an object. In another embodiment, the hanging drop can be formed at the tip of a syringe. In certain embodiments, the hanging drop is formed by using a 16, 18, or 26 gauge syringe needle. In some embodiments, the syringe can be rinsed prior to use with ultrapure deionized water and dried with nitrogen.

In some embodiments, method 200 further includes measuring a property of the hanging drop (step 204). In certain embodiments, the property is the interfacial tension. In one embodiment, the interfacial tension can be determined by analyzing the geometry of the hanging drop. The adsorption of the polymerase at the droplet interface can be measured, thereby indicating the capability of the surfactant to reduce the loss of polymerase in a droplet or emulsion PCR reaction.

FIG. 3 illustrates an exemplary hanging droplet 300 in accordance with certain non-limiting embodiments of the present invention. Hanging drop 300 comprises $D_e$ 301, which is the largest equatorial width of hanging drop 300. Hanging drop 300 further comprises $D_s$ 302, which is defined as the width of hanging drop 300 at a distance of $D_e$ from the bottom of hanging drop 300. The shape, S, of the hanging drop can be determined based on the largest equatorial width, $D_e$ 301, and the width $D_s$ 302. The shape, S, of hanging drop 300 can be measured as $D_s/D_e$.

In one embodiment, the interfacial tension can be determined using the above described measurements. The interfacial tension can be determined using the following Equation I:

$$\gamma = 3.17 g \Delta p D_e^{-0.68} D_s^{2.68}.$$

In Equation 1, $D_e$ is the largest equatorial width of the hanging drop, $D_s$ is the width of the hanging drop at a distance $D_e$ from the bottom of the hanging drop, g is the acceleration due to gravity, 9.8 m/s², and $\Delta p$ is the difference in density between the aqueous droplet and the oil phase.

In some embodiments, the interfacial tension can be measured over time. In one embodiment, the interfacial tension is measured immediately after formation of the hanging drop. In some embodiments, the interfacial tension is measured at subsequent points in time. In some embodiments, a steady state interfacial tension is measured. A steady state interfacial tension can be an interfacial tension, which no longer changes over time within a certain degree of error. By measuring the interfacial tension of a hanging drop over time, the adsorption of surfactants and proteins to a surface can be indirectly examined. Interfacial tension between the continuous phase and droplet phase decreases proportionally to the number of amphiphiles bound to the surface. Thus, a decrease in interfacial tension over time is indicative of an increase in the adsorption of surfactants and proteins. In a PCR reaction mixture, surfactants and proteins can compete for the surface. A continuous decrease in interfacial tension over time can be indicative of an increase in protein adsorption, which has a negative effect on PCR. A small decrease (or absence of a decrease) in interfacial tension over time is indicative of a surfactant that has a higher capability and/or efficiency for droplet or emulsion PCR. Thus, in some embodiments of the present invention, the use of a surfactant that results in a small decrease (or the absence of a decrease) in interfacial tension over time is desirable. In some embodiments, a difference in interfacial tension between the initial interfacial tension measurement and the steady state interfacial tension measurement of about 1.0 dyne/cm is indicative of a low amount of protein adsorption, which is preferential for droplet or emulsion PCR. In certain embodiments, the difference in interfacial tension is about 0.75 dyne/cm, about 0.50 dyne/cm, about 0.25 dyne/cm, or less than about 0.25 dyne/cm.

In some embodiments, the measured property of the hanging drop is the surface pressure. In one embodiment, the surface pressure can be measured using Equation II:

$$d\Pi/dt = k_f \nu C e^{-\Pi \Delta A/kT} - k_r \nu C^* e^{-\Pi \Delta A/kT}.$$

In Equation II, $k_f$ and $k_r$ are the adsorption and desorption rate constant, $\nu$ is the number of adsorbing groups, C and C* are the bulk and surface concentration of the species in the same units, $\Delta A$ is the area created in the film to adsorb the species, and $\Pi \Delta A$ is the work required to create space of size $\Delta A$ in a film under surface pressure $\Pi$.

When the adsorption of the species is irreversible, the surface pressure can be measured using Equation III:

$$\ln(d\Pi/dt) = \ln(k_f \nu C) - \Pi \Delta A/kT.$$

In Equation III, $k_f$ is the adsorption and desorption rate constant, $\nu$ is the number of adsorbing groups, C is the bulk concentration of the species, $\Pi A$ is the area created in the film to adsorb the species, and $\Pi \Delta A$ is the work required to create space of size $\Delta A$ in a film under surface pressure $\Pi$.

In another aspect, the present invention provides a kit for performing droplet or emulsion PCR. In some embodiments, the kit comprises a surfactant having Formula 1:

R—(OCH$_2$CH$_2$)$_n$—OH, wherein R is an alkyl group consisting of 12 to 18 carbons and n is 2 to 25. In other embodiments, the kit includes instructions for performing a test. In certain embodiments, the kit can also contain common reagents necessary for PCR such as polymerases, primers, dNTPs, buffers, salts, etc. Such reagents are known to persons of ordinary skill in the art.

EXAMPLES

The present invention is described by reference to the following Examples, which are offered by way of illustration and are not intended to limit the invention in any manner. Standard techniques well known in the art or the techniques specifically described below were utilized.

Example 1

Materials and Chemicals: Mineral oil and Brij L4® purchased from Sigma-Aldrich Corporation (St. Louis, Mo.) and ABIL EM90 obtained from Evonik Industries (Germany). Microfluidic chips and PCR wells were fabricated from Sylgard 184 PDMS. PCR master mix consisted of Taq polymerase (Bio-Rad, Hercules, Calif.), PCR buffer (200 mM Tris-HCl, pH 8.4, 500 mM KCl), magnesium chloride, an equimolar deoxynucleotide mix, and LC Green (BioFire Diagnostics, Inc., Salt Lake City, Utah). pUC 19 plasmid (Thermo, Waltham, Mass.) was utilized as the DNA template for PCR. The plasmid was amplified using a forward primer with sequence ACA GAG TTC TTG AAG TGG TGG (SEQ ID NO. 1), and a reverse primer with sequence TGG TTT GTT TGC CGG GAT CAA (SEQ ID NO. 2), where were purchased from Integrated DNA Technologies (Coralville, Iowa).

Example 2

Interfacial Tension Measurement: Interfacial tension measurements were taken using the pendant drop technique. Drop shape factors, $D_e$, taken as the largest width of the drop and, $D_s$, taken as the width of the drop at a distance of $D_e$ from the bottom of the drop as shown in FIG. 3, were empirically correlated to the interfacial tension γ using Equation I:

$$\gamma = 3.17 g \Delta p D_e^{-0.68} D_s^{2.68},$$

where g is the acceleration due to gravity, 9.8 m/s$^2$, and Δp is the difference in density between the aqueous droplet and the oil phases. See A. W. Adamson, Physical Chemistry of Surfaces, 3rd ed., Wiley, New York, 1976.

Stock mineral oil solutions of 1.5% (w/w) ABIL EM90, 0.5% (w/w) Brij L4, and unaltered mineral oil were stored at room temperature. Aqueous solutions of Taq consisting of 20 mM Tris-HCl, 50 mM KCl, and 1.5 mM MgCl$_2$ were made the day of experiments and stored on ice. The concentration of Taq Pol in the aqueous droplet phase ranged from 0 to 8×, wherein 1× was 0.025 U/µL. Hanging aqueous droplets were formed in mineral oil solutions using 16, 18, or 26 gauge syringe needles to form the largest non-spherical droplets without pinching off. No difference was seen in γ by using different sized syringe needles. Syringes were rinsed out thoroughly with ultrapure deionized water (18.2 MΩ) and dried with nitrogen between experiments. Mineral oil solutions were preheated and maintained at 55° C. with a water bath during all experiments to obtain measurements at relevant elevated PCR temperatures. Interfacial tensions for each time point were calculated from 5 images of the pendant droplet using a Pulnix TM-1405GE CCD. See P. E. Rueger et al., Chem. Eng. Res. Des. All of the equipment was setup on a vibration isolation table to minimize droplet movement, with the exception of the CCD, which was stabilized on a tripod. Each experimental condition was observed for at least 1 hour and conducted in triplicate. The maximum error in γ at each time point was 0.1 dyne/c, and the maximum error from drop to drop was 0.5 dyne/cm.

Figure 4:
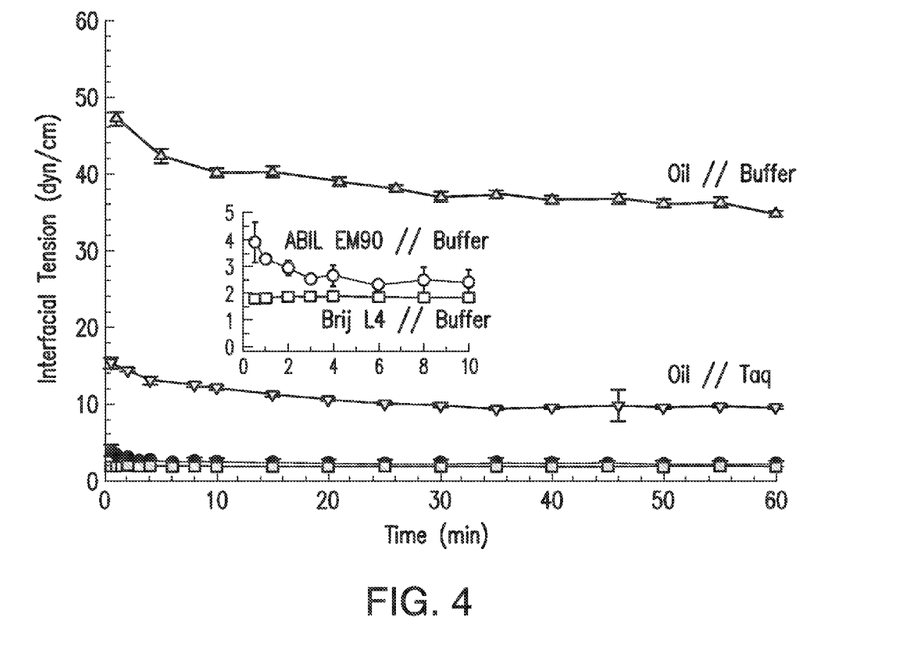
FIG. 4 is a graph of interfacial tension (dyne/cm) versus time (min) of solutions comprising mineral oil, Taq Pol, ABIL EM90, and Brij L4® in accordance with an embodiment of the present invention.

The adsorption of Taq Pol, ABIL EM90, and Brij L4® were studied indirectly by measuring the interfacial tension over time using the pendant drop technique. FIG. 4 depicts the interfacial tension (dyne/cm) as a function of time (minutes). In FIG. 4, the upward triangles represent an unaltered mineral oil and aqueous solution without Taq Pol (oil control), the downward triangles represent an unaltered mineral oil and 1× Taq Pol (Taq control), the circles represent a 1.5% ABIL EM90 mineral oil and aqueous solution (ABIL control), and the squares represent a 0.5% Brij L4® mineral oil and aqueous solution (Brij control). The inset in FIG. 4 depicts the interfacial tension of the ABIL control and Brij control over the first ten minutes.

As depicted in FIG. 4, the interfacial tension of (i) unaltered mineral oil and aqueous solution without Taq Pol (oil control), (ii) 1.5% ABIL EM90 mineral oil and aqueous solution (ABIL control), and (iii) unaltered mineral oil and 1× Taq Pol (Taq control) solution all decreased as a function of time. In contrast, the interfacial tension of 0.5% Brij L4® mineral oil and aqueous solution (Brij control) was constant over time.

The steady state interfacial tension of the oil control, $\gamma_O$, was equal to 36.4±0.5 dyne/cm and was used as the reference for surface pressure, Π, which is equal to $\gamma_O$–γ. Initially, γ of the ABIL Control was 3.8±0.7 dyne/cm and reached a steady state interfacial tension, $\gamma_{AO}$, of 2.17±0.07 dyne/cm within 45 minutes. The Taq control was initially 15.3±0.7 dyne/cm and decreased to a steady state of 9.6±0.1 dyne/cm within 45 minutes. The steady state interfacial tension of the Brij control, $\gamma_{BO}$, was measured to be 1.82±0.02 dyne/cm.

Adsorption dynamics of surfactants and Taq Pol at relevant PCR concentrations and time scales are not diffusion controlled. Diffusion kinetics are only valid at low surface pressures, which were never observed on the timescale of the experiments disclosed herein. During droplet formation, a surfactant or protein film was formed within seconds to milliseconds, whereby the interfacial tension drastically decreased immediately. The initial surface pressure of the Taq Control was 21.1±0.9 dyne/cm. Over time the surface pressure increased to 26.8±0.5 dyne/cm, indicating that Taq irreversibly denatures and adsorbs to the surface. The initial surface pressure of the ABIL Control was 32.6±0.9 dyne/cm. In this case, the surface pressure increases to 34.2±0.5 dyne/cm, indicating that the interface was not completely saturated and ABIL EM90 continued to bind to open sites within the surfactant film. The surface pressure of the Brij control remained constant through the experiment at 34.6±0.5 dyne/cm. This signifies that the surface was saturated immediately, and binding sites within the film were not available.

Figure 5:
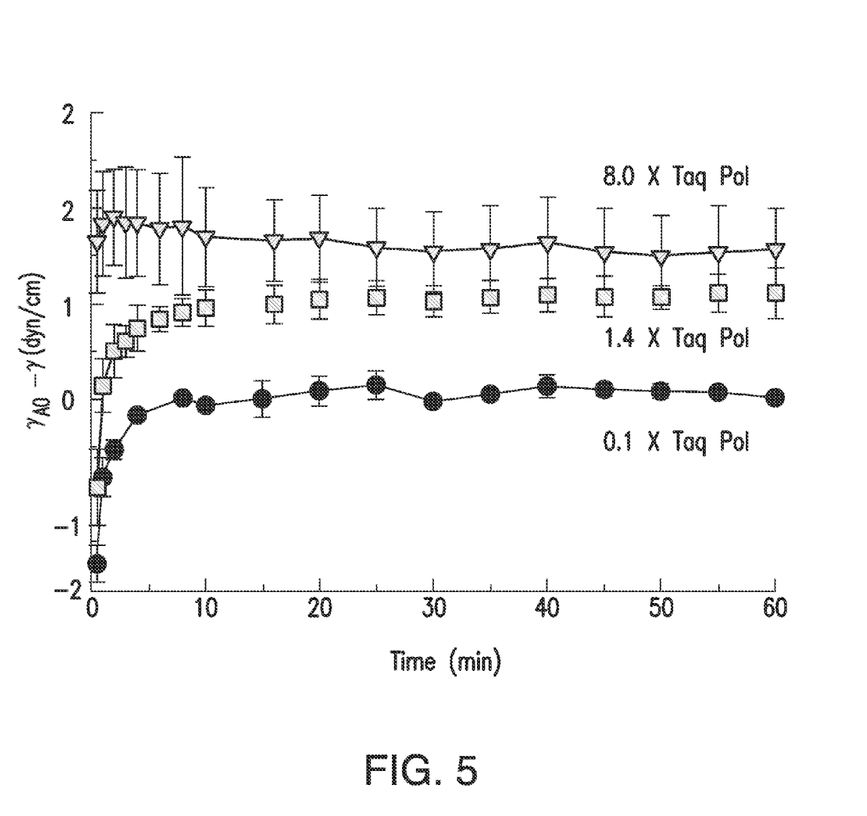
FIG. 5 is a graph of dynamic pseudo surface pressure measurements with surfactant and Taq as the deviation from the steady state surface tension with surfactant and without Taq for a 1.5% ABIL EM90 solution (dyne/cm) as a function of time (min) in accordance with an embodiment of the present invention.
Figure 6:
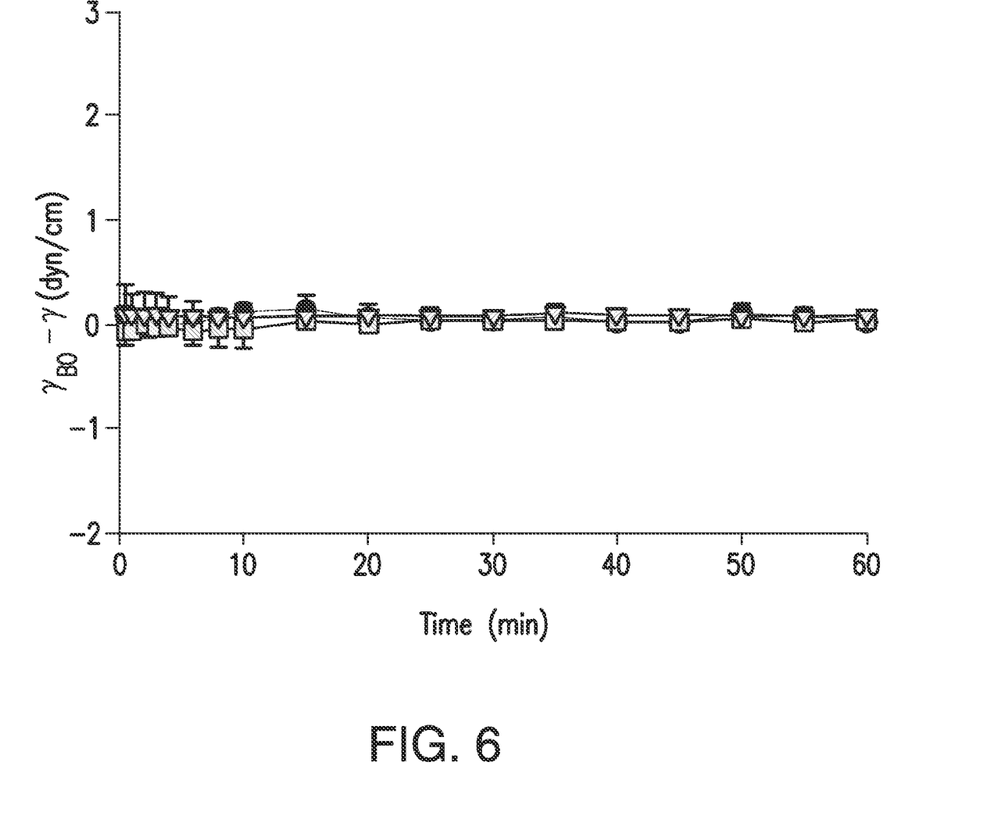
FIG. 6 is a graph of dynamic pseudo surface pressure measurements with surfactant and Taq as the deviation from the steady state surface tension with surfactant and without Taq for a 0.5% Brij L4® solution (dyne/cm) as a function of time (min) in accordance with an embodiment of the present invention.

FIG. 5 and FIG. 6 depict dynamic pseudo surface pressure measurements for 2 phase systems with surfactant and Taq are shown as the deviation from the steady state surface tension with surfactant and without Taq for 1.5% ABIL EM90 ($\gamma_{A0}-\gamma$) and 0.5% Brij L4® ($\gamma_{B0}-\gamma$), respectively. In FIG. 5 and FIG. 6, the circles represent solutions comprising 0.1× (0.0025 U/μL) Taq Pol, the squares represent solutions comprising 1.4× (0.035 U/μL) Taq Pol, and the triangles represent solutions comprising 8.0× (0.20 U/μL) Taq Pol. Initial pseudo surface pressures were negative for Taq concentrations less than 0.035 U/μL in 1.5 wt % ABIL EM90 but reached a stable plateau greater than or equal to zero within 45 minutes. At higher Taq concentrations in 1.5 wt % ABIL EM90, initial pseudo surface pressures were positive and also reached a steady state within 45 minutes. No change in pseudo surface pressures was seen in 0.5 wt % Brij L4® with all measured concentrations of Taq Pol and were stable over time, suggesting that the surface was immediately saturated, and no further adsorption occurred over time.

The kinetics of adsorption at liquid-liquid interfaces with significant excess surface concentrations of an ampiphile have been studied by Ward and Tordai. See A. F. H Ward and L. Tordai, Recl. Tray. Chim. Pays-Bas 1952, 71, 572-584. The Ward and Tordai rate equation is set forth in Equation II:

$$d\Pi/dt = k_f \nu C e^{-\Pi \Delta A/kT} - k_r \nu C^* e^{-\Pi \Delta A/kT}.$$

Equation II captures the energetic barrier of binding to a crowded interface in the case of adsorption limited kinetics where $k_f$ and $k_r$ are the adsorption and desorption rate constant, $\nu$ is the number of adsorbing groups, C and C* are the bulk and surface concentration of the species in the same units, $\Delta A$ is the area created in the film to adsorb the species, and $\Pi \Delta A$ is the work required to create space of size $\Delta A$ in a film under surface pressure $\Pi$.

When the adsorption of the species is irreversible, Equation II simplifies to Equation III:

$$\ln(d\Pi/dt) = \ln(k_f \nu C) - \Pi \Delta A/kT.$$

Figure 7:
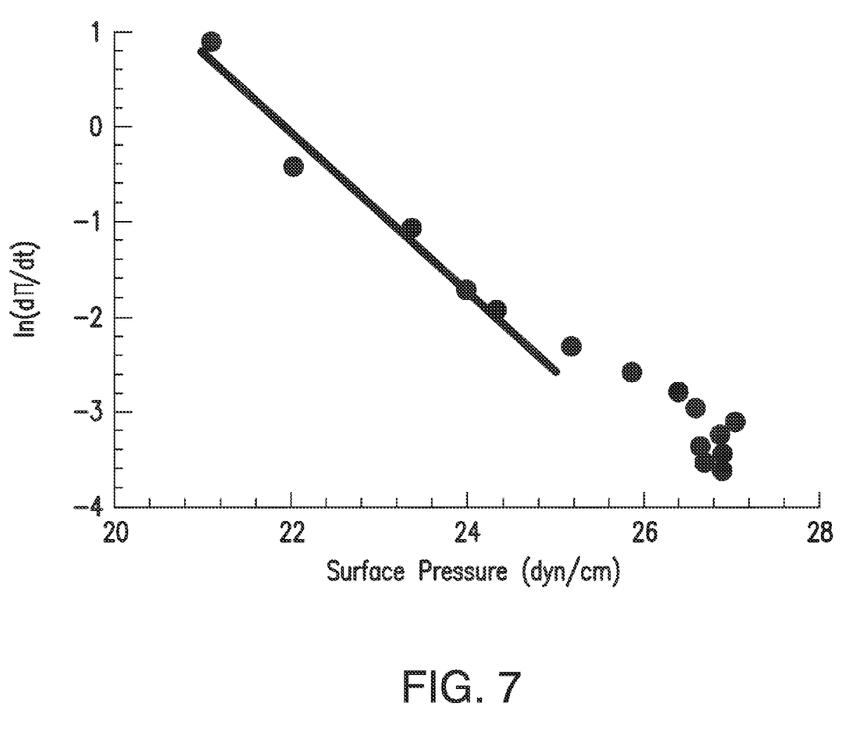
FIG. 7 is a graph of ln(dΠ\dt) as a function of surface pressure (dyne/cm) of a Taq solution in accordance with an embodiment of the present invention.

FIG. 7 depicts the term $\ln(d\Pi/dt)$ for 1× Taq and mineral oil as a function of $\Pi$. In FIG. 7, the circles represent the dynamic interfacial measurements of the 1× Taq and mineral oil solution. Linear portions in the curve with different slopes are representative of the different areas required for making a small space in the film for absorption and for making a larger space in the film for a protein to surface denature. See E. Tornberg, J. Colloid Interface Sci. 1978, 64, 391-402. In FIG. 7, the black line represents the initial linear portion of the curve at the lower surface pressure, which was fitted to Equation III where $\Delta A$ was found to be 4±1 nm² and corresponds to penetration of Taq into the film. This penetration area was comparable to that of β-lactoglobulin, a much smaller protein. The smaller penetration area relative to the size of Taq Pol was most likely due to its large hydrophobic content. Once a small portion of Taq Pol was bound, the entire protein interacted with the interface quickly. The linear portion at higher surface pressures corresponds with the area required for denaturing and spreading of Taq in the film, where $\Delta A$ was found to be 55±30 nm². The area β-lactoglobulin required for molecular rearrangement was an order of magnitude smaller. A sizeable portion of Taq Pol is hydrophobic, which would have a larger footprint when denatured than proteins of similar or smaller size.

Since adsorption begins during droplet formation, it is desirable to block the hydrophobic surface immediately to prevent proteins from binding at the interface. Using ABIL EM90, the interface does not saturate quickly, which would allow protein adsorption to occur during droplet formation and well downstream of droplet formation. A cleared area of only 4±1 nm² in the film would be required for Taq to penetrate and adsorb in the film, which is similar to the 2 nm² required by BSA—a smaller protein. See E. Tornburg supra. Brij L4® would be a superior surfactant, minimizing protein adsorption during droplet formation, because it completely saturates the surface immediately.

Figure 8:
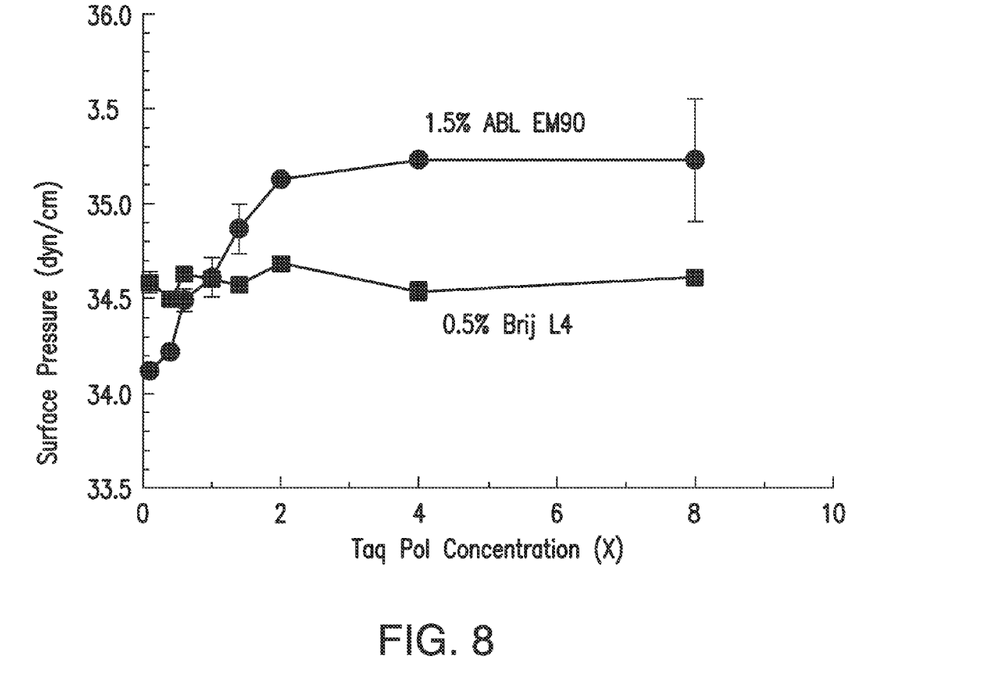
FIG. 8 is a graph of surface pressure (dyne/cm) as a function of Taq Pol concentration (X) of a 1.5% ABIL EM90 solution and a 0.5% Brij L4® solution in accordance with an embodiment of the present invention.

Brij L4® was shown to be a better surfactant than ABIL EM90 to immediately block the interface by the steady state surface pressure measurements with Taq Pol in the system. FIG. 8 depicts the change of surface of pressure, $\Pi$, with increasing Taq Pol concentration. In FIG. 8, the circles represent the surface pressure in dyne/cm as a function of the Taq Pol concentration (×) of the ABIL control. In FIG. 8, the squares represent the surface pressure in dyne/cm as a function of the Taq Pol concentration (×) of the Brij control. The initial positive slope of the ABIL EM90 curve of surface pressure with Taq Pol concentration indicated that upon droplet formation, the fresh interface adsorbed both Taq Pol and ABIL EM90, and therefore the initial amount of protein adsorbed increased as Taq concentration increased. It was not until 4× Taq Pol was in solution that the interface began to fully saturate at $\Pi$ of 35.23±0.03 dyne/cm. In picoliter droplets, however, at a concentration of 4× Taq Pol, much of the enzyme would be adsorbed and non-functional, and thus PCR could not be applied. In the case of Brij L4®, $\Pi$ remained constant at 34.59±0.02 dyne/cm over all measured Taq concentrations, indicating significant protein adsorption was prevented. Initial Taq adsorption onto a fresh droplet interface was minimized by the immediate saturating surface coverage of Brij L4®. As a result, PCR would be expected to operate successfully, even at standard Taq concentrations.

Example 3

DROPLET PCR: The PCR master mix consisted of 20 mM Tris-HCl, 50 mM KCl, 1.5 mM MgCl$_2$, 200 μM of each dNTPs, 1× LC Green, and varying concentrations of Taq Pol. The initial concentration of pUC-19 was 5×10$^6$ copies/μL. Wells were fabricated by creating holes in 2.5 mm thick cured PDMS using a 5 mm biopsy punch. Individual wells were separated and bonded to cover glass slips; bonding of the PDMS to glass was performed by spinning PDMS at 3000 rpm for 30 s on the glass to form a thin layer that served as an adhesive. Aqueous droplets 20±2 μm in diameter (approximately 4 pL) were formed in the PDMS microfluidic chips using a flow focusing geometry and then captured in wells filled with mineral oil solutions. Care was taken to capture single droplets in well when using Brij L4® as the surfactant due to droplet coalescence during thermocycling. Wells were sealed with cover glass slips before thermocycling on an aluminum plate heated and cooled with a peltier.

Aqueous droplets were initially hot started at 95° C. for 3 minutes, then thermocycled for 35 cycles. Each thermocycle consisted of 30 seconds at 55° C. for annealing, 30 seconds at 72° C. for extension, and 30 seconds at 95° C. for melting. Real time amplification results were obtained after every extension step by exciting droplets using a blue LED (Innovations in Optics, Woburn, Mass.) with a Brightline 424-438 nm bandpass filter, while capturing fluorescence emission with a CCD (Allied Vision, Stradtroda, Germany) fitted with a high pass filter (475 nm cut-off) (Omega Optica, Brattleboro, Vt.). The cycle threshold was defined as the cycle where the fluorescence during extension of a given cycle was greater than the fluorescence during the extension of the first cycle by 10 standard deviations.

Confirmation of Brij L4® as a superior surfactant for PCR was performed with 4 pL droplet thermocycling and real time fluorescence measurements. At the 4 pL droplet size, the number of initial copies of pUC-19 per droplet varies probabilistically but with an average of 25 initial plasmids. Therefore, the cycle threshold of real-time qPCR experiments would vary. Though initial plasmid copy numbers per droplet were low, fluorescence of droplets with LC Green at room temperature was clearly distinguishable from the background (though at 72° C., the initial fluorescence was nearly indistinguishable from the background).

In each cycle of PCR, primers hybridize to template DNA to form a partially double stranded segment and are subsequently extended by Taq Pol. If the PCR is efficient, all bound primers are extended every cycle and the copies of the PCR product sequence defined by the primers (i.e., amplicons) roughly doubles every cycle. This is achieved if sufficient active Taq Pol is in solution to catalyze the extension of all bound primers. An excess of Taq Pol in solution would have no effect on the cycle threshold, whereas a depletion of Taq Pol would decrease the cycle efficiency of PCR and thus increase the cycle threshold.

Figure 9:
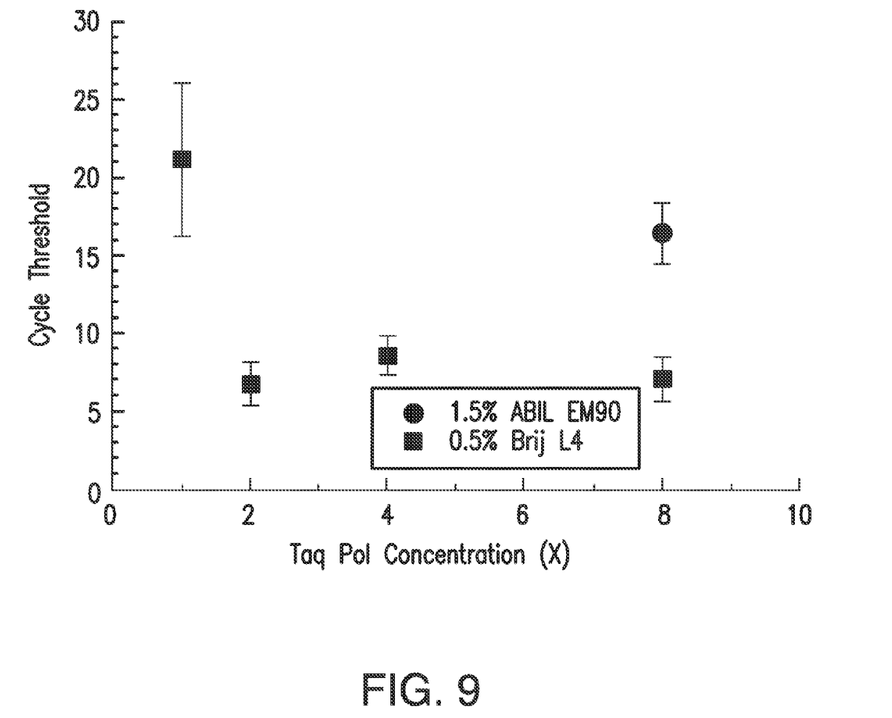
FIG. 9 is a graph of the cycle threshold as a function of the Taq Pol concentration (X) of PCR reaction mixtures comprising 1.5% ABIL EM90 and 0.5% Brij L4® in accordance with an embodiment of the present invention.

FIG. 9 depicts the cycle threshold as a function of Taq Pol concentration. In FIG. 9, the circle represents a PCR mixture comprising 1.5% ABIL EM90 and the square represents a PCR mixture comprising 0.5% Brij L4®. As illustrated in FIG. 9, the PCR cycle efficiency of 0.5% Brij L4® was drastically better than the PCR cycle efficiency of 1.5 wt % ABIL EM90 in picoliter droplets. Using 1.5% ABIL EM90 and 8× Taq Pol, 16±2 cycles were necessary to reach the fluorescence threshold. Blocking the hydrophobic interface with 0.5% Brij L4® resulted in much more efficient PCR, with a cycle threshold of 7±1.5 cycles at the same Taq Pol and initial pUC-19 concentration. While sufficient Taq Pol was in solution with ABIL EM90 to amplify DNA, much more was available using Brij L4®. Furthermore, using less than 8× Taq Pol with ABIL EM90 resulted in Taq Pol concentrations below a critical level sufficient to perform PCR. Efficient PCR was achieved with Taq Pol concentrations as low as 2× with Brij L4® with a cycle threshold of 7±1.5 cycles. Though an efficient number of cycles were necessary to reach a fluorescence threshold using Brij L4®, copies of the DNA sequence defined by the primers would increase by a factor of approximately 60 if all bound primers were extended. DNA amplification was still achieved using 1× Taq Pol with 0.5% Brij L4®, 21±5 cycles were necessary to reach the fluorescence threshold. The sharp increase indicates that in fact a fraction of Taq Pol is absorbed during droplet formation, but that using a concentration of 2× Taq Pol is sufficient to completely overcome this lost Taq Pol.

Successful PCR with Brij L4® also confirms that surfactant was not completely degraded during thermocycling. Although, droplet coalescence was observed when using Brij L4®, this would only be an issue in PCR emulsion experiments, and it could be circumvented by using a combination of ABIL EM90 and Brij L4®. With this combination, the interface would still be saturated immediately. The majority of the film would be composed of Brij L4® and Taq Pol adsorption would be minimized; ABIL EM90 would make up a lesser portion but still prevent droplet coalescence.

The surfactant Brij L4® was shown to be a surprisingly superior surfactant than conventional surfactants used in droplet or emulsion PCR, such as ABIL EM90. As little as 1× Taq Pol was used for amplification of droplet PCR mixtures with Brij L4®, which was much less than the concentration of Taq Pol required for amplification of droplet PCR mixtures with conventional surfactants. It was observed that Brij L4® immediately saturates the interface, and therefore, minimizes Taq Pol adsorption during droplet formation.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the methods described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

We claim:

1. A droplet or emulsion polymerase chain reaction (PCR) mixture comprising:
   an aqueous droplet comprising a polymerase chain reaction mixture;
   an oil phase, wherein the aqueous droplet is surrounded by the oil phase; and
   a surfactant having Formula I: R—(OCH$_2$CH$_2$)$_n$—OH,
   wherein R is an alkyl group consisting of 12 to 18 carbons and n is 2 to 25, wherein the surfactant is selected from the group consisting of ceteth-2, ceteth-20, ceteareth-12, ceteareth-20, ceteareth-25, steareth-2, steareth-10, steareth-20, steareth-21, oleth-2, oleth-5, oleth-10, and oleth-20.

2. The droplet or emulsion PCR mixture of claim 1, wherein the polymerase chain reaction mixture comprises a polymerase, a primer, nucleotides, and a template nucleic acid.

3. The droplet or emulsion PCR mixture of claim 2, wherein the polymerase is Taq polymerase.

4. The droplet or emulsion PCR mixture of claim 1, wherein the oil phase comprises mineral oil.

5. The droplet or emulsion PCR mixture of claim 1, wherein the aqueous droplet is surrounded by the oil phase and the surfactant.

6. A method for preparing a mixture for droplet or emulsion polymerase chain reaction ("PCR") comprising:
   forming an aqueous droplet comprising a polymerase chain reaction mixture;
   surrounding the aqueous droplet with an oil phase;
   adding a surfactant having Formula I: R—(OCH$_2$CH$_2$)$_n$—OH,
   wherein R is an alkyl group consisting of 12 to 18 carbons and n is 2 to 25, wherein the surfactant is selected from the group consisting of ceteth-2, ceteth-20, ceteareth-12, ceteareth-20, ceteareth-25, steareth-2, steareth-10, steareth-20, steareth-21, oleth-2, oleth-5, oleth-10, and oleth-20.

7. The method of claim 6, wherein the polymerase chain reaction mixture comprises a polymerase, a primer, nucleotides, and a template nucleic acid.

8. The method of claim 7, wherein the polymerase is Taq polymerase.

9. The method of claim 6, wherein the oil phase comprises mineral oil.

10. The method of claim 6, wherein the surfactant is added to the oil phase.

11. The method of claim 6, wherein the surfactant is added to the oil phase before aqueous droplet is surrounded by the oil phase.

12. The method of claim 6, wherein the surfactant is added after the aqueous phase is surrounded by the oil phase.

13. The method of claim 6, further comprising hot starting the aqueous droplet.

14. The method of claim 6, further comprising thermocycling the aqueous droplet.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Sequence -  Forward Primer

<400> SEQUENCE: 1
acagagttct tgaagtggtg g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Sequence - Reverse Primer

<400> SEQUENCE: 2
tggtttgttt gccgggatca a                                              21
```